United States Patent [19]

Kost et al.

[11] Patent Number: 5,413,690
[45] Date of Patent: May 9, 1995

[54] POTENTIOMETRIC BIOSENSOR AND THE METHOD OF ITS USE

[75] Inventors: Kent M. Kost; Thomas J. Lindsay, both of Fishers; John F. Price, McCordsville, all of Ind.

[73] Assignee: Boehringer Mannheim Corporation, Indianapolis, Ind.

[21] Appl. No.: 97,331

[22] Filed: Jul. 23, 1993

[51] Int. Cl.$^6$ .......................................... G01N 27/26
[52] U.S. Cl. ..................... 204/403; 204/412; 204/418; 204/435; 435/817; 435/288; 435/291
[58] Field of Search ............... 204/403, 412, 418, 435, 204/433; 435/817, 288, 291

[56] References Cited

U.S. PATENT DOCUMENTS

| | | | |
|---|---|---|---|
| 4,340,448 | 7/1982 | Schiller et al. | 204/403 |
| 4,552,840 | 11/1985 | Riffer | 204/403 |
| 4,713,165 | 12/1987 | Conover et al. | 204/403 |
| 4,844,910 | 7/1989 | Leslie et al. | 424/494 |
| 4,966,671 | 10/1990 | Nylander et al. | 204/418 |
| 5,120,420 | 6/1992 | Nankai et al. | 204/403 |
| 5,264,103 | 11/1993 | Yoshioka et al. | 204/403 |

*Primary Examiner*—Kathryn Gorgos
*Assistant Examiner*—Bruce F. Bell

[57] ABSTRACT

A potentiometric biosensor, test strip, reagent and a potentiometric method for detection or measurement of an analyte from a fluid sample. The biosensor includes indicating and reference electrodes, and a reagent, which overlays a portion of the surface of the indicating electrode. The reagent generally includes an enzyme and a redox mediator. When a fluid sample (e.g., blood) containing an analyte (e.g., glucose) is added to the reagent, the enzyme (e.g., glucose oxidase) catalyzes a reaction involving enzyme, redox mediator (e.g., potassium ferricyanide), and analyte.

This reaction may be monitored by monitoring the electrical potential at the indicating electrode surface. (Electrical potential at the indicating electrode surface changes as the concentration of oxidized and reduced forms of the redox mediator change at the indicating electrode surface.) The inventive potentiometric biosensor measures the change in potential at the indicating electrode surface after the fluid sample containing the analyte is added to the reagent. The change in potential that occurs may be correlated to the detection or measurement of analyte in the fluid sample.

17 Claims, 2 Drawing Sheets

POTENTIOMETRIC BIOSENSOR AND THE METHOD OF ITS USE

FIELD OF THE INVENTION

The invention relates to the assay of an analyte by a potentiometric biosensor.

BACKGROUND OF THE INVENTION

Potentiometric biosensors are known. Conover et al., U.S. Pat. No. 4,713,165 (issued Dec. 15, 1987), discloses a sensor having ion selective electrodes. The sensor includes three cells, each cell having a reference half-cell (including a reference electrode and a reference fluid) and a measuring half-cell. The half-cells are separated by an ion selective membrane, and each half-cell is connected to an adjacent measuring half-cell by a porous material that permits ionic flow. The measuring half-cell may further include a membrane which includes an enzyme, an enzyme substrate, or an antigen. Generally, a sample that contains an analyte of interest is added to a measuring half-cell. A reaction sequence is set up to generate some ion (for example, ammonium ion or hydronium ion). Therefore, the activity of the ion in the measuring half-cell changes. The change in potential of the measuring half-cell versus the reference half-cell reflects the change in activity in the measuring half-cell.

When a reference solution and a calibrating solution are added to the other measuring half-cells, the change in potential in the sample-containing half-cell may be correlated to the amount of analyte in the sample.

Schiller et al., U.S. Pat. No. 4,340,448 (issued Jul. 20, 1982), discloses a potentiometric device for the assay of an analyte. The device has a working electrode and a reference electrode. An oxidase enzyme is immobilized on the working electrode. The working electrode must be made of a material, such as platinum, capable of measuring potential as a function of the change in the concentration of hydrogen peroxide. For example, a sample containing glucose may be added to the device, wherein the working electrode includes glucose oxidase (and may also include catalase). The change in potential reflects the production of hydrogen peroxide, produced by the following reaction:

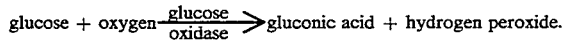

The change in potential may be correlated to the concentration of glucose in the sample.

Riffer, U.S. Pat. No. 4,552,840 (issued Nov. 12, 1985), discloses an enzyme electrode for the analysis of dextran.

The electrode, from exterior to interior, comprises a sheath (cellulose sheath) including dextranase, a dialysis membrane (optional), a sheath including α-glucosidase, a sheath including glucose oxidase, and a platinum redox electrode. The electrode is immersed into a sample, containing an unknown amount of dextran and a known added amount of ferrocyanide (an excess). Dextran is hydrolyzed (by the enzymes in the various sheaths) to glucose. Glucose is oxidized to gluconic acid, and molecular oxygen is reduced to hydrogen peroxide. Ferrocyanide is oxidized by hydrogen peroxide and is used as an indicator of the peroxide generated. Potential changes as ferrocyanide is oxidized to ferricyanide. The change in potential is correlated to the concentration of dextran in the sample.

Nylander et al., U.S. Pat. No. 4,966,671 (issued Oct. 30, 1990), discloses a potentiometric analysis method, wherein a sample, containing an unknown amount of analyte (e.g., potassium), is added to each of two chambers. Each chamber includes an electrode (usually, similar electrodes, e.g., silver/silver chloride). The chambers are separated by a partition that permits ionic flow but is impermeable to the analyte being measured. One chamber includes a known amount of the analyte to be measured. When the sample to be measured is added to each chamber, the difference in concentration of analyte between the chambers creates a potential difference. The magnitude of the potential difference is a function of the amount of analyte in the sample.

None of these references discloses a simple potentiometric biosensor and assay method, wherein the analyte sought to be measured is anaerobically oxidized or reduced in an assay involving an enzyme, a redox mediator, and the analyte; and changes in system potential, which result from changes in the ratio of oxidized/reduced form of the redox mediator, are directly correlated to the detection or measurement of the analyte in the assay.

SUMMARY OF THE INVENTION

The invention is a potentiometric biosensor, test strip, reagent, and a potentiometric method for detection or measurement of an analyte from a fluid sample. The biosensor includes indicating and reference electrodes, and a reagent, which overlays a portion of the surface of the indicating electrode. The reagent includes an enzyme and a redox mediator. When a fluid sample (e.g., blood) containing an analyte (e.g., glucose) is added to the reagent, the enzyme (e.g., glucose oxidase) catalyzes a reaction involving enzyme, redox mediator (e.g., potassium ferricyanide), and analyte. This reaction may be illustrated for the analysis of glucose as follows:

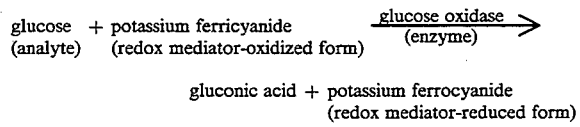

When the reagent overlays a portion of the indicating electrode surface, the above reaction affects the electrical potential measured at the indicating electrode surface. The effect is described by the Nernst equation, $$E = E^\circ + \frac{RT}{nF} \ln (C^\circ_{ox}/C^\circ_{red}),$$

wherein
E = Potential at the indicating electrode surface
E° = Formal potential of the redox couple (the oxidized and reduced forms of the redox mediator)
R = Universal Gas Constant
T = Temperature
n = Number of electrons transferred in the chemical reaction
F = Faraday Constant
$C^\circ_{ox}$ = Concentration or activity of the oxidized form of the redox mediator at the indicating electrode surface
$C^\circ_{red}$ = Concentration or activity of the reduced form of the redox mediator at the indicating electrode surface Therefore, the above reaction may be monitored by observing the potential at the indicating electrode surface, which changes as the ratio of $C°_{ox}/C°_{red}$ changes. The inventive potentiometric biosensor measures the change in potential of the system as a result of the chemical reaction of analyte/enzyme/mediator. That change in potential may be correlated to the detection or measurement of analyte in the fluid sample.

The potentiometric biosensor may operate by utilizing a test strip that includes an electrically insulative base, indicating and reference electrodes supported on the base, and an overlay of insulating material, which includes a cutout portion that exposes surfaces of the indicating and reference electrodes. Overlaying the indicating electrode in the cutout portion is a reagent of known amount. The reagent generally includes an enzyme and redox mediator, and preferably includes a buffer, a dispersant and crystallization inhibitor, a thickener, and a surfactant. A potentiometer in electrical connection with the indicating and reference electrodes is used to measure changes in potential that occur at the indicating electrode surface in response to the enzyme, analyte, redox mediator reaction.

In operation, a fluid sample containing the analyte of interest is added to the reagent, thereby forming a test sample. The ensuing reaction of enzyme, analyte, and redox mediator produces a measurable change in potential at the surface of the indicating electrode. This measurable change in potential may be correlated to the detection or measurement of the amount of analyte in the fluid sample.

DETAILED DESCRIPTION OF THE INVENTION

Figure 1:
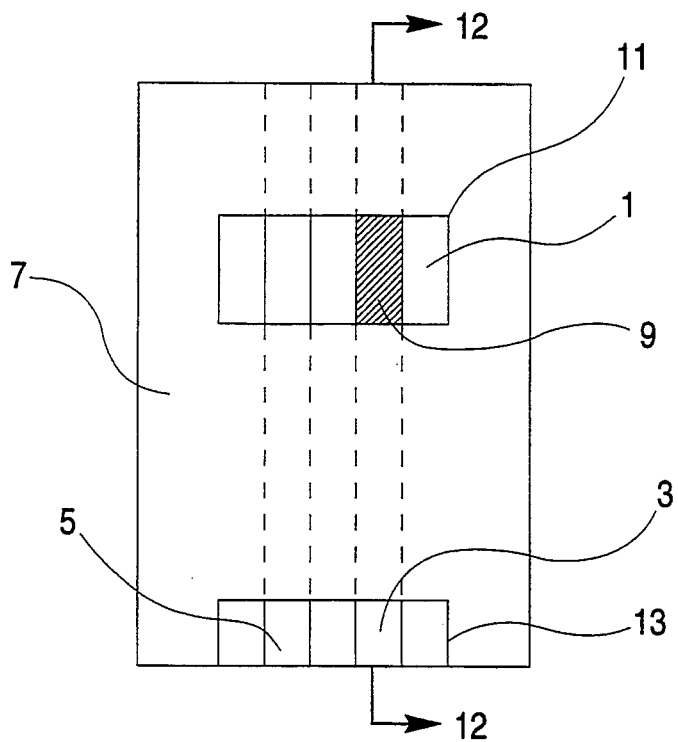
FIG. 1 is a top view of an embodiment of the test strip for use in the potentiometric biosensor.

The potentiometric biosensor may be used to analyze analytes involved in the following general reaction scheme:

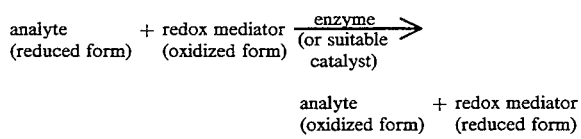

This general reaction scheme may be specifically illustrated for the analysis of glucose as follows:

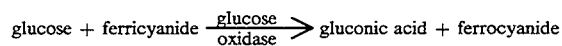

Electrical potential in the above systems may be correlated to the detection or measurement of the analyte in the system because electrical potential is defined by the following equation (Nernst Equation):

$$E = E° + \frac{RT}{nF} \ln(C°_{ox}/C°_{red}),$$

E = Potential at the indicating electrode surface

E° = Formal potential of the redox couple (the oxidized and reduced forms of the redox mediator)

R = Universal Gas Constant

T = Temperature n = Number of electrons transferred in the chemical reaction

F = Faraday Constant $C°_{ox}$ = Concentration or activity of the oxidized form of the redox mediator at the indicating electrode surface $C°_{ox}$ = Concentration or activity of the reduced form of the redox mediator at the indicating electrode surface As can be seen from the above equation, the system potential changes as the reaction progresses because the redox mediator is being converted from its oxidized form to its reduced form in the above examples. While the redox mediator is being reduced, analyte is being oxidized. As a result, changes in system potential, which directly result from the changing ratio $C°_{ox}/C°_{red}$, may be correlated to the concentration of analyte in the fluid sample. The potentiometric biosensor utilizes this phenomenon to detect or measure the amount of analyte from a fluid sample.

The potentiometric biosensor generally includes the following elements:

a. an indicating electrode;

b. a reference electrode;

c. a reagent of known amount overlaying a portion of the surface of the indicating electrode and comprising an enzyme and a redox mediator, the enzyme being of sufficient type and in sufficient amount to catalyze a reaction involving the enzyme, the redox mediator, and an analyte from a fluid sample, the redox mediator being in sufficient amount such that the reaction involving the enzyme, the redox mediator, and the analyte produces a measurable change in potential, at the surface of the indicating electrode, that is substantially attributable to the change in proportions of the oxidized and reduced forms of the redox mediator; and d. a potentiometer in electrical connection with the indicating and reference electrodes.

More generally, the potentiometric biosensor could be utilized as a potentiometric sensor. The analyte to be measured could be a non biological analyte; therefore, a catalyst other than an enzyme could be used. Further, if the analyte would react directly with the redox mediator, then no catalyst would be required.

A reference electrode, such as a silver/silver chloride reference electrode, is required so that measurements of potential will be accurately made with respect to a fixed reference point. The indicating electrode may be made of any electrically conducting material, such as palladium, platinum, gold, silver, titanium, copper, and carbon. It is important that the reagent overlay a portion of the surface of the indicating electrode so that potential difference measurements may be made at the indicating electrode surface. It is also important that the reagent contain a known amount of redox mediator. Because analyte determinations are made based upon measurements of system potential, which is determined by $C°_{ox}/C°_{red}$, error in the amount of redox mediator included in the reagent will cause error in determination of the amount of analyte from a fluid sample.

The choice of enzyme and redox mediator utilized in the reagent for the biosensor will depend upon the analyte being measured. Exemplary analyte, enzyme, and redox mediator combinations are given below in Table I.

TABLE 1

| ANALYTE | ENZYME | REDOX MEDIATOR (OXIDIZED FORM) | ADDITIONAL MEDIATOR |
|---|---|---|---|
| Glucose | Glucose Dehydrogenase and Diaphorase | Ferricyanide | |
| Cholesterol | Cholesterol Esterase and Cholesterol Oxidase | Ferricyanide | 2,6-Dimethyl, 1,4-Benzoquinone 2,5-Dichloro-1,4-Benzoquinone |
| HDL Cholesterol | Cholesterol Esterase and Cholesterol Oxidase | Ferricyanide | 2,6-Demethyl-1,4-Benzoquinone 2,5-Dichloro-1,4-Benzoquinone or phenazine ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide, Phenazine Ethosulfate, or Phenazine Methosulfate | |
| Lactate Dehydrogenase | Diaphorase | Ferricyanide, Phenazine Ethosulfate, or Phenazine Methosulfate | |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table I, at least one additional enzyme is used as a reaction catalyst. Also, some of the examples shown in Table I may utilize an additional mediator, which facilitates electron transfer to the oxidized form of the redox mediator. The additional mediator may be provided to the reagent in lesser amount than the oxidized form of the redox mediator.

The amount of enzyme included in the reagent may vary depending upon the time desired for completion of the reaction involving enzyme, analyte, and redox mediator. In general, if more enzyme is added, then the shorter the time period for completion of the reaction. Other factors, such as pH and ionic strength, can also influence the kinetics of this reaction.

Maximum sensitivity of measurement of an analyte will be achieved when the amount of redox mediator in the reagent is sufficient to be nearly completely converted from one form (e.g., the oxidized form) to the other form (e.g., the reduced form) by the reaction involving analyte, enzyme, and redox mediator. A nearly complete change in the redox mediator from one form to the other will most greatly change the system electrical potential, as shown by the Nernst Equation.

Preferably, the biosensor reagent includes a dispersant and crystallization inhibitor, such as AVICEL RC-591F, a blend of 88% microcrystalline cellulose and 12% carboxymethylcellulose (available from FMC Corp.), and a thickener, such as NATROSOL-250 M (a microcrystalline hydroxyethylcellulose available from Aqualon). Other preferred reagent components include a buffer and a surfactant. The buffer should be of sufficient type and in sufficient amount to provide and maintain a pH at which the enzyme catalyzes the reaction involving the enzyme, the redox mediator, and the analyte. The surfactant should be of sufficient type and in sufficient amount to aid wetting of the reagent by a fluid sample (such as blood).

The reagent could be incorporated in a test strip for use in the potentiometric biosensor. The test strip would include the following elements:

a. a first electrical insulator;
b. indicating and reference electrodes supported on the first electrical insulator;
c. a second electrical insulator, overlaying the first electrical insulator and the electrodes and including a cutout portion that exposes surface areas of the indicating and reference electrodes; and
d. a known amount of biosensor reagent overlaying the exposed surface of the indicating electrode in the cutout portion.

Figure 2:
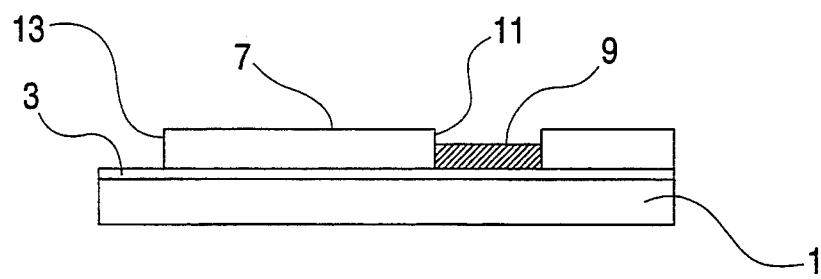
FIG. 2 is a cross-sectional view of the biosensor shown in FIG. 1 along lines 12—12.

A possible construction for the biosensor strip is shown in FIGS. 1 and 2, which depict the following elements: first electrical insulator 1, indicating electrode 3, reference electrode 5, second electrical insulator 7, reagent 9, cutout portion 11, and additional cutout portion 13. (Additional cutout portion 13 is included for easy electrical connection of a potentiometer to the indicating and reference electrodes.)

First electrical insulator 1, and second electrical insulator 7, may be made of an insulative plastic, such as vinyl polymer or polyimide plastic, or other useful electrically insulating material.

Indicating electrode 3 may be made of palladium, gold, copper, platinum, carbon, silver, titanium, or other useful electrically conducting material.

Reference electrode 5 may be a silver/silver chloride electrode, a saturated calomel electrode, or other suitable reference electrode. Further, electrodes 3 and 5 may be affixed to insulator 1, and insulator 1 maybe affixed to insulator 7, by the use of hot melt adhesive.

A protocol for making a reagent 9 that could be added to cutout portion 11 and used for the analysis of glucose from a blood sample is as follows:

Step 1—Prepare 1 liter (in a volumetric flask) of a buffer/NATROSOL mixture by adding 1.2000 grams (g) NATROSOL-250 M to 0.740 molar (M) aqueous potassium phosphate buffer (including 80.062 g monobasic potassium phosphate and 26.423 g dibasic potassium phosphate) at pH 6.25. Allow the buffer/NATROSOL mixture to stir and swell for 3 hours.

Step 2—Prepare an AVICEL mixture by stirring 14.000 g AVICEL RC-591 F and 504.7750 g water for 20 minutes.

Step 3—Prepare a TRITON mixture by adding 0.5000 g TRITON X-100 surfactant to 514.6000 g of the buffer/NATROSOL mixture and stir for 15 minutes.

Step 4—While stirring, add the total TRITON mixture dropwise with a dropwise addition funnel or buret to the total AVICEL mixture. Once addition is complete, continue stirring overnight.

Step 5—To the mixture resulting from Step 4, add, while stirring, about 25 g potassium ferricyanide. (Add a little potassium ferricyanide at a time to allow the potassium ferricyanide to dissolve as added.)

Step 6—Stir the resulting mixture of Step 5 for 20 minutes.

Step 7—Adjust the pH of the mixture resulting from Step 6 to 6.25 by adding potassium hydroxide.

Step 8—To the resulting mixture of Step 7 add 9.1533 g glucose oxidase (218.50 units per milligram (mg) from Biozyme) and stir at least 20 minutes.

Step 9—To the resulting mixture of Step 8 add 6 g disodium succinate and stir at least 20 minutes.

Step 10—Filter the resulting mixture of Step 9 through a 100 micron sieve bag to remove AVICEL clumping. The filtrate is the resulting reagent composition, which is added to at least the indicating electrode surface in cutout portion 11 and is then dried.

For glucose determination, 6 microliters (μl) of reagent made by the above-stated protocol should be added to at least the indicating electrode surface in cutout portion 11. This amount of reagent will contain a sufficient amount of ferricyanide, and a sufficient amount of enzyme (glucose oxidase) to catalyze the oxidation of glucose (from a sample of human whole blood) and the reduction of ferricyanide to completion within about 20 seconds.

Reagent 9 is then dried by heating at about 50° C. for about 3 minutes. After drying, a polyester or nylon mesh may be placed on top of the dried reagent to aid in preventing loss of reagent from the biosensor during shipping and handling and to aid in minimizing human contamination from reagent 9. The mesh may be affixed to substrate 7 by adhesive tape.

To illustrate the principle of operation of the potentiometric biosensor, a palladium indicating electrode and a silver/silver chloride reference electrode, both in electrical connection with a potentiometer, were exposed to solutions of varying ferricyanide/ferrocyanide ratios. As shown below in Table II, varying the ratio of ferricyanide/ferrocyanide resulted in a change in potential at the indicating electrode surface. These results indicate that changes in the oxidized/reduced form of the redox mediator can be used to detect or measure the amount of an analyte from a fluid sample.

TABLE II

| S1 = Potassium Ferricyanide Solution(aqueous) = 0.09 molar(M) | | |
|---|---|---|
| S2 = Potassium Ferrocyanide Solution(aqueous) = 0.09M | | |
| E (millivolts) | S1 (microliters) | S2 (microliters) |
| Test #1 - | | |
| 440 | 20 | 0 |
| 297 | 16 | 4 |
| 258 | 12 | 8 |
| 255 | 10 | 10 |
| 243 | 8 | 12 |
| 209 | 4 | 16 |
| 80 | 0 | 20 |
| Test #2 (one day after Test #1) - | | |
| 439 | 20 | 0 |
| 322 | 18 | 2 |
| 299 | 16 | 4 |
| 265 | 12 | 8 |
| 249 | 10 | 10 |
| 239 | 8 | 12 |
| 211 | 4 | 16 |

TABLE II-continued

| S1 = Potassium Ferricyanide Solution(aqueous) = 0.09 molar(M) | | |
|---|---|---|
| S2 = Potassium Ferrocyanide Solution(aqueous) = 0.09M | | |
| E (millivolts) | S1 (microliters) | S2 (microliters) |
| 110 | 0 | 20 |

The detection or measurement of an analyte from a fluid sample could be conducted by employing the following steps:

a. forming a test sample by adding the fluid sample (e.g., a blood sample) to the biosensor, wherein the reagent is fully exposed to the fluid sample and fluid sample contacts both the indicating and reference electrodes, thereby forming a circuit;

b. incubating the test sample a sufficient period of time to produce a measurable change in potential, which is substantially attributable to the change in proportions of the oxidized and reduced forms of the redox mediator, at the surface of the indicating electrode (The incubation period may be fixed at some period of time greater than the minimum time required to produce a measurable change in potential.);

c. measuring potential after the incubation period; and d. correlating the measured potential to the detection or measurement of the analyte from the fluid sample.

For measurement of glucose from human whole blood, a 20 μl sample of human whole blood may be added to cutout portion 11, thereby combining with reagent 9 and forming the test sample. (The sample volume of human whole blood must be sufficient to wet reagent 9 and to connect electrodes 3 and 5 in cutout 11.) The test sample may be incubated at ambient room temperature for about 20 seconds, or some other fixed period of time equal to or greater than the minimum time required to produce a measurable change in potential at the surface of the indicating electrode, and potential at the surface of the indicating electrode (relative to the reference electrode) measured. The measured potential is then correlated to the amount of glucose (or the detection of glucose) in the blood sample by comparing like measurements with glucose solutions of known concentration.

The potentiometric biosensor described above has several advantages. First, the potentiometric biosensor would be very inexpensive, requiring only a test strip like the one described above and an inexpensive potentiometer. Second, the potentiometric biosensor would be subject to fewer interferences than an amperometric biosensor. For example, in an amperometric biosensor, unwanted electroactive species will contribute to the measured current, thereby causing error in the assay. However, in the potentiometric biosensor, potential changes only as a result of the changing ratios of oxidized and reduced forms of the redox mediator. (Both amperometric and potentiometric biosensors would be subject to error from unwanted chemical reactions that remove either the oxidized or reduced form of the redox mediator from the assay system. For example, in a glucose assay, ferricyanide might chemically be reduced to ferrocyanide by uric acid rather than being reduced in the reaction involving glucose, ferricyanide, and glucose oxidase.) Third, in the potentiometric biosensor there is no dependence on the size of the indicating electrode. Fourth, the potentiometric biosensor would produce a rapid assay because potential measurements could be made as soon as a measurable change in potential was achieved at the surface of the indicating electrode.

Figure 3:
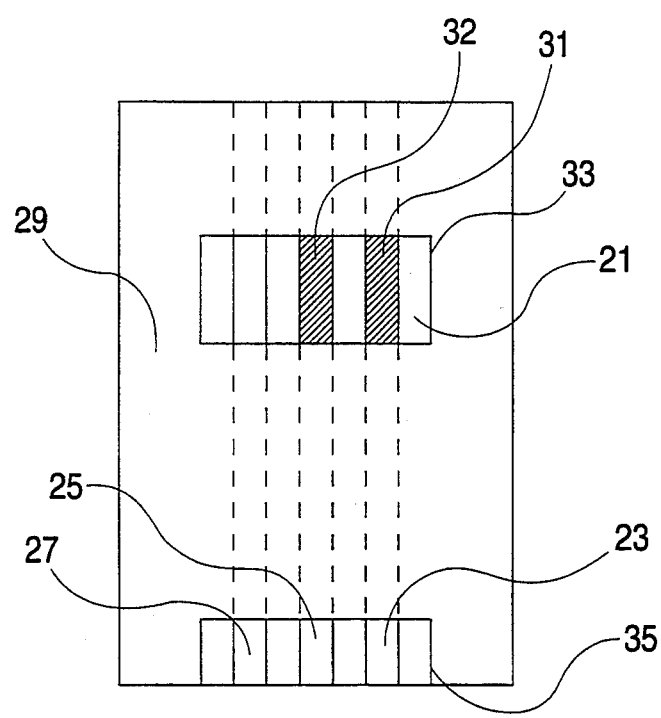
FIG. 3 is a top view of another embodiment of the test strip for use in the potentiometric biosensor.

While a two electrode potentiometric biosensor, having an indicating electrode and a reference electrode, has been illustrated, the potentiometric biosensor may have multiple indicating electrodes. For example, FIG. 3 illustrates a three electrode potentiometric biosensor strip, which includes first electrical insulator 21, first indicating electrode 23, second indicating electrode 25, reference electrode 27, second electrical insulator 29, first reagent 31, second reagent 32, cutout portion 73, and additional cutout portion 35. For example, first reagent 31 could be the reagent described above for detecting or measuring glucose in a fluid sample, and reagent 32 could be a reagent for detecting or measuring one of the other analytes listed in Table 1.

Further, assays have been illustrated, wherein the analyte is oxidized and the redox mediator is reduced in the assay. However, the potentiometric biosensor also applies to assays wherein the analyte is enzymatically reduced and the redox mediator is oxidized.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

We claim:

1. A potentiometric biosensor for analysis of an analyte from a fluid sample, comprising:
   a. an indicating electrode;
   b. a reference electrode;
   c. a reagent of known amount overlaying a portion of the surface of the indicating electrode and comprising a redox mediator,
   the redox mediator being in an amount to react with all of the analyte at the surface of the indicating electrode, thereby causing a measurable change in potential that correlates to the change in proportions of the oxidized and reduced forms of the redox mediator at the surface of the indicating electrode; and
   d. a potentiometer in electrical connection with the indicating and reference electrodes.

2. A potentiometric biosensor, comprising:
   a. an indicating electrode;
   b. a reference electrode;
   c. a reagent of known amount overlaying a portion of the surface of the indicating electrode and comprising a catalyst and a redox mediator,
   the catalyst being in an amount to catalyze a reaction involving the catalyst, the redox mediator, and an analyte from a fluid sample,
   the redox mediator being in an amount to react with all of the analyte at the surface of the indicating electrode, thereby causing a measurable change in potential that correlates to the change in proportions of the oxidized and reduced forms of the redox mediator at the surface of the indicating electrode; and
   d. a potentiometer in electrical connection with the indicating and reference electrodes.

3. A potentiometric biosensor, comprising:
   a. an indicating electrode;
   b. a reference electrode;
   c. a reagent of known amount overlaying a portion of the surface of the indicating electrode and comprising an enzyme and a redox mediator,
   the enzyme being in an amount to catalyze a reaction involving the enzyme, the redox mediator, and an analyte from a fluid sample,
   the redox mediator being in an amount to react with all of the analyte at the surface of the indicating electrode, thereby causing a measurable change in potential that correlates to the change in proportions of the oxidized and reduced forms of the redox mediator at the surface of the indicating electrode; and
   d. a potentiometer in electrical connection with the indicating and reference electrodes.

4. A potentiometric method of detecting an analyte from a fluid sample, comprising the steps of:
   a. forming a test sample by adding the fluid sample to the potentiometric biosensor of claim 1, wherein the reagent is fully exposed to the fluid sample and the fluid sample contacts both the indicating and the reference electrodes, thereby forming a circuit;
   b. incubating the test sample to produce the measurable change in potential that correlates to the change in proportions of the oxidized and reduced forms of the redox mediator at the surface of the indicating electrode;
   c. measuring potential after incubation; and
   d. correlating the measured potential to detection of the analyte.

5. A potentiometric method of measuring an analyte from a fluid sample, comprising the steps of:
   a. forming a test sample by adding the fluid sample to a potentiometric biosensor including,
      1) a first electrical insulator,.
      2) indicating and reference electrodes supported on the first electrical insulator,
      3) a second electrical insulator, overlaying the first electrical insulator and the electrodes and including a cutout portion that exposes surface areas of the indicating and reference electrodes,
      4) a reagent of known amount overlaying the exposed surface of the indicating electrode in the cutout portion and comprising a redox mediator,
      the redox mediator being in sufficient amount to react with all of the analyte at the surface of the indicating electrode, thereby causing a measurable change in potential that correlates to the change in proportions of the oxidized and reduced forms of the redox mediator at the surface of the indicating electrode, and
      5) a potentiometer in electrical connection with the indicating and reference electrodes,
   wherein the reagent is fully exposed to the fluid sample and the fluid sample contacts both the indicating and reference electrodes, thereby forming a circuit;
   b. incubating the test sample to produce the measurable change in potential that correlates to the change in proportions of the oxidized and reduced forms of the redox mediator at the surface of the indicating electrode;
   c. measuring potential after incubation; and
   d. correlating the measured potential to the amount of the analyte in the fluid sample.

6. A potentiometric method of detecting an analyte from a fluid sample, comprising the steps of:

a. forming a test sample by adding the fluid sample to the potentiometric biosensor of claim 2, wherein the reagent is fully exposed to the fluid sample and the fluid sample contacts both the indicating and the reference electrodes, thereby forming a circuit;
b. incubating the test sample to produce the measurable change in potential that correlates to the change in proportions of the oxidized and reduced forms of the redox mediator at the surface of the indicating electrode;
c. measuring potential after incubation; and
d. correlating the measured potential to detection of the analyte.

7. A potentiometric method of measuring an analyte from a fluid sample, comprising the steps of:
   a. forming a test sample by adding the fluid sample to a potentiometric biosensor including,
      1) a first electrical insulator,
      2) indicating and reference electrodes supported on the first electrical insulator,
      3) a second electrical insulator, overlaying the first electrical insulator and the electrodes and including a cutout portion that exposes surface areas of the indicating and reference electrodes,
      4) a reagent of known amount overlaying the exposed surface of the indicating electrode in the cutout portion and comprising a catalyst, a buffer, and a redox mediator,
      the catalyst being in an amount to catalyze a reaction involving the catalyst, the redox mediator, and an analyte from the fluid sample,
      the buffer being in an amount to provide and maintain a pH at which the catalyst catalyzes the reaction involving the catalyst, the redox mediator, and the analyte,
      the redox mediator being in an amount to react with all of the analyte at the surface of the indicating electrode, thereby causing a measurable change in potential that correlates to the change in proportions of the oxidized and reduced forms of the redox mediator at the surface of the indicating electrode, and
      5) a potentiometer in electrical connection with the indicating and reference electrodes,
      wherein the reagent is fully exposed to the fluid sample and the fluid sample contacts both the indicating and reference electrodes, thereby forming a circuit;
   b. incubating the test sample to produce the measurable change in potential that correlates to the change in proportions of the oxidized and reduced forms of the redox mediator at the surface of the indicating electrode;
   c. measuring potential after incubation; and
   d. correlating the measured potential to the amount of the analyte in the fluid sample.

8. A potentiometric method of detecting an analyte from a fluid sample, comprising the steps of:
   a. forming a test sample by adding the fluid sample to a potentiometric biosensor including,
      1) a first electrical insulator,
      2) indicating and reference electrodes supported on the first electrical insulator,
      3) a second electrical insulator, overlaying the first electrical insulator and the electrodes and including a cutout portion that exposes surface areas of the indicating and reference electrodes,
      4) a reagent of known amount overlaying the exposed surface of the indicating electrode in the cutout portion and comprising an enzyme, a buffer, and a redox mediator,
      the enzyme being in an amount to catalyze a reaction involving the enzyme, the redox mediator, and an analyte from the fluid sample,
      the buffer being in an amount to provide and. maintain a pH at which the enzyme catalyzes the reaction involving the enzyme, the redox mediator, and the analyte,
      the redox mediator being in an amount to react with all of the analyte at the surface of the indicating electrode, thereby causing a measurable change in potential that correlates to the change in proportions of the oxidized and reduced forms of the redox mediator at the surface of the indicating electrode, and
      5) a potentiometer in electrical connection with the indicating and reference
      wherein the reagent is fully exposed to the fluid sample and the fluid sample contacts both the indicating and reference electrodes, thereby forming a circuit;
   b. incubating the test sample to produce the measurable change in potential that correlates to the change in proportions of the oxidized and reduced forms of the redox mediator at the surface of the indicating electrode;
   c. measuring potential after incubation; and
   d. correlating the measured potential to the detection of the analyte.

9. A potentiometric method of measuring an analyte from a fluid sample, comprising the steps of:
   a. forming a test sample by adding the fluid sample to a potentiometric biosensor including,
      1) a first electrical insulator,
      2) indicating and reference electrodes supported on the first electrical insulator,
      3) a second electrical insulator, overlaying the first electrical insulator and the electrodes and including a cutout portion that exposes surface areas of the indicating and reference electrodes,
      4) a reagent of known amount overlaying the exposed surface of the indicating electrode in the cutout portion and comprising an enzyme, a buffer, and a redox mediator,
      the enzyme being in an amount to catalyze reaction involving the enzyme, the redox mediator, and an analyte from the fluid sample,
      the buffer being in an amount to provide and maintain a pH at which the enzyme catalyzes the reaction involving the enzyme, the redox mediator, and the analyte,
      the redox mediator being in an amount to react with all of the analyte at the surface of the indicating electrode, thereby causing a measurable change in potential that correlates to the change in proportions of the and reduced forms of the redox mediator at the surface of the indicating electrode, and
      5) a potentiometer in electrical connection with the indicating and reference electrodes,
      wherein the reagent is fully exposed to the fluid sample and the fluid sample contacts both the indicating and reference electrodes, thereby forming a circuit;

b. incubating the test sample to produce the measurable change in potential that correlates to the change in proportions of the oxidized and reduced forms of the redox mediator at the surface of the indicating electrode;

c. measuring potential after incubation; and d. correlating the measured potential to the amount of the analyte in the fluid sample.

10. A potentiometric method of measuring an analyte from a fluid sample, comprising the steps of:

a. forming a test sample by adding the fluid sample to the potentiometric biosensor of claim 3, wherein the reagent is fully exposed to the fluid sample and the fluid sample contacts both the indicating and reference electrodes, thereby forming a circuit;

b. incubating the test sample to produce the measurable change in potential that correlates to the change in proportions of the oxidized and reduced forms of the redox mediator at the surface of the indicating electrode;

c. measuring potential after incubation; and d. correlating the measured potential to the amount of the analyte in the fluid sample.

11. A potentiometric biosensor for analysis of an analyte from a fluid sample, comprising:

a. a first electrical insulator;

b. indicating and reference electrodes supported on the first electrical insulator;

c. a second electrical insulator, overlaying the first electrical insulator and the electrodes and including a cutout portion that exposes surface areas of the indicating and reference electrodes;

d. a reagent of known amount overlaying the exposed surface of the indicating electrode in the cutout portion and comprising a redox mediator, the redox mediator being in an amount to react with all of the analyte at the surface of the indicating electrode, thereby causing a measurable change in potential that correlates to the change in proportions of the oxidized and reduced forms of the redox mediator at the surface of the indicating electrode; and e. a potentiometer in electrical connection with the indicating and reference electrodes.

12. The potentiometric biosensor of claim 11, wherein the reagent further comprises a dispersant and crystallization inhibitor and a thickener.

13. A potentiometric biosensor, comprising:

a. a first electrical insulator;

b. indicating and reference electrodes supported on the first electrical insulator;

c. a second electrical insulator, overlaying the first electrical insulator and the electrodes and including a cutout portion that exposes surface areas of the indicating and reference electrodes;

d. a reagent of known amount overlaying the exposed surface of the indicating electrode in the cutout portion and comprising a catalyst and a redox mediator, the catalyst being in an amount to catalyze a reaction involving the catalyst, the redox mediator, and an analyte from a fluid sample, the redox mediator being in an amount to react with all of the analyte at the surface of the indicating electrode, thereby causing a measurable change in potential that correlates to the change in proportions of the oxidized and reduced forms of the redox mediator at the surface of the indicating electrode; and e. a potentiometer in electrical connection with the indicating and reference electrodes.

14. The potentiometric biosensor of claim 13, wherein the reagent further comprises a buffer in sufficient amount to provide and maintain a pH at which the catalyst catalyzes the reaction involving the catalyst, the redox mediator, and the analyte.

15. A potentiometric biosensor, comprising:

a. a first electrical insulator;

b. indicating and reference electrodes supported on the first electrical insulator;

c. a second electrical insulator, overlaying the first electrical insulator and the electrodes and including a cutout portion that exposes surface areas of the indicating and reference electrodes;

d. a reagent of known amount overlaying the exposed surface of the indicating electrode in the cutout portion and comprising an enzyme and a redox mediator, the enzyme being in an amount to catalyze a reaction involving the enzyme, the redox mediator, and an analyte from a fluid sample, the redox mediator being in an amount to react with all of the analyte at the surface of the indicating electrode, thereby causing a measurable change in potential that correlates to the change in proportions of the oxidized and reduced forms of the redox mediator at the surface of the indicating electrode; and e. a potentiometer in electrical connection with the indicating and reference electrodes.

16. The potentiometric biosensor of claim 15, wherein the reagent further comprises a buffer in an amount to provide and maintain a pH at which the enzyme catalyzes the reaction involving the enzyme, the redox mediator, and the analyte.

17. The potentiometric biosensor of claim 15, wherein the indicating electrode is selected from a group consisting of palladium, platinum, gold, silver, titanium, copper, and carbon.

* * * * *